United States Patent [19]

Smith

[11] 4,167,625
[45] Sep. 11, 1979

[54] TRANS-4,5,13,14-TETRADEHYDRO-PGI$_1$ AMIDES

[75] Inventor: Herman W. Smith, Kalamazoo Township, Kalamazoo County, Mich.

[73] Assignee: The Upjohn Company, Kalamazoo, Mich.

[21] Appl. No.: 915,350

[22] Filed: Jun. 14, 1978

Related U.S. Application Data

[63] Continuation-in-part of Ser. No. 821,536, Aug. 3, 1977.

[51] Int. Cl.$^2$ ............................................. C07D 307/93
[52] U.S. Cl. .................................... 542/430; 542/418; 260/346.73; 542/421; 542/429; 542/431

[58] Field of Search .................. 260/346.73; 542/431, 542/418, 421, 429, 430

[56] References Cited

PUBLICATIONS

Johnson et al., J.A.C.S., 99:12, Jun. 1977, pp. 4182–4184.

Primary Examiner—John M. Ford
Assistant Examiner—Bernard Dentz
Attorney, Agent, or Firm—Robert A. Armitage

[57] ABSTRACT

The present invention relates to certain structural and pharmacological analogs of prostacyclin (PGI$_2$) which are trans-4,5,13,14-tetradehydro-PGI$_1$ amides. These novel pharmacological agents are useful as smooth muscle stimulators.

30 Claims, No Drawings

TRANS-4,5,13,14-TETRADEHYDRO-PGI$_1$ AMIDES

CROSS REFERENCE TO RELATED APPLICATION

The present application is a continuation-in-part of Ser. No. 821,536, filed Aug. 3, 1977, now pending.

The present invention relates to prostacyclin analogs, for which the essential material constituting disclosure therefor is incorporated by reference here from Ser. No. 821,541, filed Aug. 3, 1977, now U.S. Pat. No. 4,109,082, issued Aug. 22, 1978.

I claim:

1. A prostacyclin analog of the formula

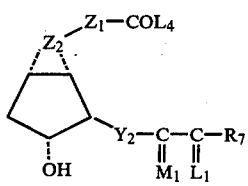

wherein Y$_2$ is —C≡C—;
wherein Z$_2$ is

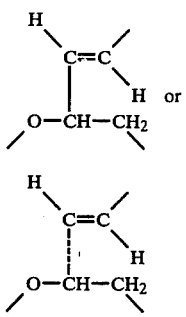

wherein Z$_1$ is
(1) —(CH$_2$)$_g$—CH$_2$—CH$_2$—, or
(2) —(CH$_2$)$_g$—CH$_2$—CF$_2$—,
wherein g is the integer zero, one, or 2;
wherein M$_1$ is

wherein R$_5$ is hydrogen or alkyl with one to 4 carbon atoms, inclusive;
wherein L$_1$ is

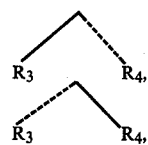

or a mixture of

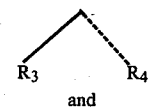

and

-continued wherein R$_3$ and R$_4$ are hydrogen, methyl, or fluoro, being the same or different, with the proviso that one of R$_3$ and R$_4$ is fluoro only when the other is hydrogen or fluoro; wherein L$_4$ is (a) amino of the formula —NR$_{21}$R$_{22}$; wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive, benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive; or nitro; pyridyl; pyridyl substituted by one, 2, or 3 chloro, alkyl of one to 3 carbon atoms, inclusive, or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms, inclusive, hydroxy, or alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of R$_{21}$ and R$_{22}$ is other than hydrogen or alkyl;

(b) cycloamino selected from the group consisting of

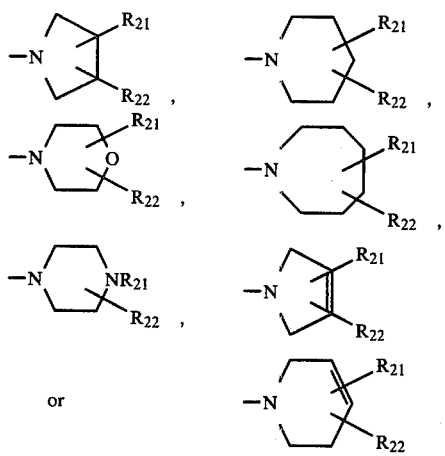

wherein R$_{21}$ and R$_{22}$ are defined above;
(c) carbonylamino of the formula —NR$_{23}$COR$_{21}$, wherein R$_{23}$ is hydrogen or alkyl of one to 4 carbon atoms and R$_{21}$ is as defined above;
(d) sulfonylamino of the formula —NR$_{23}$SO$_2$R$_{21}$, wherein R$_{21}$ and R$_{23}$ are as defined above; or
(e) hydrazino of the formula —NR$_{23}$R$_{24}$, wherein R$_{23}$ is as defined above and R$_{24}$ is amino of the formula —NR$_{21}$R$_{22}$, as defined above; and wherein $R_7$ is (1) $—(CH_2)_m—CH_3$,

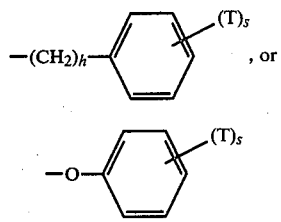

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Z_2$ is a mixture of

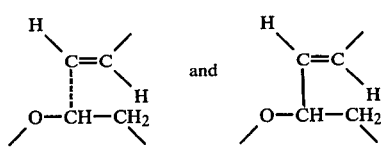

3. (6RS)-trans-4,5,13,14-Tetradehydro-PGI$_1$, amide, a prostacyclin analog according to claim 2.

4. A prostacyclin analog according to claim 1, wherein $Z_2$ is

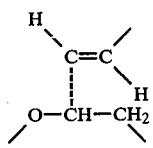

5. trans-4,5,13,14-Tetradehydro-6α-PGI$_1$, amide, a prostacyclin analog according to claim 4.

6. 15-Methyl-trans-4,5,13,14-tetradehydro-6α-PGI$_1$, amide, a prostacyclin analog according to claim 4.

7. 16,16-Dimethyl-trans-4,5,13,14-tetradehydro-6α-PGI$_1$, amide, a prostacyclin analog according to claim 4.

8. 16,16-Difluoro-trans-4,5,13,14-tetradehydro-6α-PGI$_1$, amide, a prostacyclin analog according to claim 4.

9. A prostacyclin analog according to claim 1, wherein $Z_2$ is

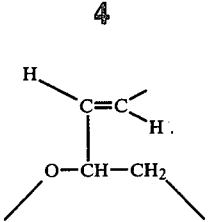

10. A prostacyclin analog according to claim 9, wherein $Z_1$ is $—(CH_2)_g—CH_2—CF_2—$.

11. 2,2-Difluoro-trans-4,5,13,14-tetradehydro-6β-PGI$_1$, amide, a prostacyclin analog according to claim 10.

12. A prostacyclin analog according to claim 9, wherein $Z_1$ is $—(CH_2)_g—CH_2—CH_2—$.

13. A prostacyclin analog according to claim 12, wherein g is zero.

14. A prostacyclin analog according to claim 13, wherein

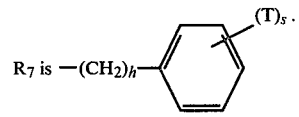

15. 17-Phenyl-18,19,20-trinor-trans-4,5,13,14-tetradehydro 6β-PGI$_1$, amide, a prostacyclin analog according to claim 14.

16. A prostacyclin analog according to claim 13, wherein

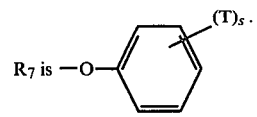

17. 16-Phenoxy-17,18,19,20-tetranor-trans-4,5,13,14-tetradehydro-6β-PGI$_1$, amide, a prostacyclin analog according to claim 16.

18. A prostacyclin analog according to claim 13, wherein $R_7$ is $—(CH_2)_m—CH_3—$.

19. A prostacyclin analog according to claim 18, wherein $R_5$ is methyl.

20. 15-Methyl-trans-4,5,13,14-tetradehydro-6β-PGI$_1$, amide, a prostacyclin analog according to claim 19.

21. A prostacyclin analog according to claim 18, wherein $R_5$ is hydrogen.

22. A prostacyclin analog according to claim 21, wherein at least one of $R_3$ and $R_4$ is fluoro.

23. 16,16-Difluoro-trans-4,5,13,14-tetradehydro-6β-PGI$_1$, amide, a prostacyclin analog according to claim 22.

24. A prostacyclin analog according to claim 21, wherein at least one of $R_3$ and $R_4$ is methyl.

25. 16,16-Dimethyl-trans-4,5,13,14-tetradehydro-6β-PGI$_1$, amide, a prostacyclin analog according to claim 24.

26. A prostacyclin analog according to claim 21, wherein $R_3$ and $R_4$ are both hydrogen.

27. trans-4,5,13,14-Tetradehydro-6β-PGI$_1$, methylsulfonyl amide, a prostacyclin analog according to claim 26.

28. trans-4,5,13,14-Tetradehydro-6β-PGI$_1$, piperidyl amide, a prostacyclin analog according to claim 26.

29. trans-4,5,13,14-Tetradehydro-6β-PGI$_1$, methyl amide, a prostacyclin analog according to claim 26.

30. trans-4,5,13,14-Tetradehydro-6β-PGI$_1$, amide, a prostacyclin analog according to claim 26.

* * * * *